(12) United States Patent
Campbell et al.

(10) Patent No.: US 8,710,295 B2
(45) Date of Patent: Apr. 29, 2014

(54) SOYBEAN SEQUENCES ASSOCIATED WITH THE FAP3 LOCUS

(75) Inventors: Matthew Campbell, Des Moines, IA (US); Jennifer A. Klaiber, Urbandale, IA (US)

(73) Assignee: Pioneer Hi-Bred International Inc, Johnston, IA (US)

( * ) Notice: Subject to any disclaimer, the term of this patent is extended or adjusted under 35 U.S.C. 154(b) by 346 days.

(21) Appl. No.: 13/103,506

(22) Filed: May 9, 2011

(65) Prior Publication Data

US 2011/0277173 A1 Nov. 10, 2011

Related U.S. Application Data

(60) Provisional application No. 61/332,928, filed on May 10, 2010.

(51) Int. Cl.
*A01H 5/10* (2006.01)
*A01H 1/02* (2006.01)

(52) U.S. Cl.
USPC ........... 800/267; 800/264; 800/312; 800/266; 435/6.11; 435/6.12

(58) Field of Classification Search
None
See application file for complete search history.

(56) References Cited

PUBLICATIONS

Kim et al. (Theor. Appl. Genet. (2005) 110: 1003-1010).*
Cardinal, et al., Estimating the Individual Effects of the Reduced Palmitic Acid fap nc and fap1 Alleles on Agronomic Traits in Two Soybean Populations, Crop Science, 2008, V48p663.
Cardinal, et al., Molecular Analysis of Soybean Lines with Low Palmitic Acid Content in Seed Oil, Crop Science, 2007, V47p304.
Li, et al., Molecular Mapping Genes Conditioning Reduced Palmitic Acid Content in N87-2122-4 Soybean, Crop Science, 2002, V42p373.
Wilson, et al., Metabolic Mechanisms Associated with Alleles Governing the 16:0 Concentration of Soybean Oil, JAOCS, 2001, V78p335.
Primomo, et al., Inheritance and Interaction of Low Palmitic and Low Linolenic Soybean, Crop Science, 2002, V42p31.
Cardinal, et al., Correlations between Palmitate Content and Agronomic Traits in Soybean Populations Segregating for the fap1, fap nc, and fan Alleles, Crop Science, 2007, V47p1804.

* cited by examiner

*Primary Examiner* — David T Fox
*Assistant Examiner* — Jared Shapiro

(57) ABSTRACT

Compositions and methods for identifying soybean plants with reduced levels of saturated fatty acids are provided. Methods of making soybean plants with reduced levels of saturated fatty acids, e.g., through introgression of desired saturated fatty acid marker alleles and/or by transgenic production methods, as well as plants or germplasm made by these methods, are provided. Kits for selecting plants with reduced levels of saturated fatty acids are also provided.

12 Claims, 6 Drawing Sheets

Figure 2A

| ID | FAP3_35a_4_1 | R160 | Phenotype |
|---|---|---|---|
| 62 | FAM | 2.3 | Low Sat |
| 29 | FAM | 2.4 | Low Sat |
| 28 | FAM | 2.4 | Low Sat |
| 65 | FAM | 2.4 | Low Sat |
| 4 | FAM | 2.5 | Low Sat |
| 15 | FAM | 2.5 | Low Sat |
| 6 | FAM | 2.5 | Low Sat |
| 55 | FAM | 2.5 | Low Sat |
| 26 | FAM | 2.5 | Low Sat |
| 36 | FAM | 2.5 | Low Sat |
| 58 | FAM | 2.5 | Low Sat |
| 69 | FAM | 2.5 | Low Sat |
| 42 | FAM | 2.5 | Low Sat |
| 1 | FAM | 2.6 | Low Sat |
| 9 | FAM | 2.6 | Low Sat |
| 63 | FAM | 2.6 | Low Sat |
| 60 | FAM | 2.6 | Low Sat |
| 59 | FAM | 2.6 | Low Sat |
| 30 | FAM | 2.6 | Low Sat |
| 57 | FAM | 2.6 | Low Sat |
| 55 | FAM | 2.6 | Low Sat |
| 19 | FAM | 2.7 | Low Sat |
| 35 | FAM | 2.7 | Low Sat |
| 95 | FAM | 2.7 | Low Sat |
| 57 | FAM | 2.8 | Low Sat |
| 38 | FAM | 2.8 | Low Sat |
| 15 | FAM | 2.8 | Low Sat |
| 8 | FAM | 2.9 | Low Sat |
| 60 | FAM | 2.9 | Low Sat |
| 19 | FAM | 2.9 | Low Sat |
| 54 | FAM | 2.9 | Low Sat |
| 8 | FAM | 2.9 | Low Sat |
| 14 | FAM | 2.9 | Low Sat |
| 30 | FAM | 3 | Low Sat |
| 4 | FAM | 3 | Low Sat |
| 11 | FAM | 3 | Low Sat |
| 31 | FAM | 3 | Low Sat |
| 70 | FAM | 3 | Low Sat |
| 98 | FAM | 3 | Low Sat |
| 27 | FAM | 3.1 | Low Sat |
| 32 | FAM | 3.1 | Low Sat |
| 11 | FAM | 3.1 | Low Sat |
| 75 | FAM | 3.1 | Low Sat |
| 74 | FAM | 3.2 | Low Sat |

Figure 2B

| ID | FAP3_35a_4_1 | R160 | Phenotype |
|---|---|---|---|
| 6 | FAM | 3.2 | Low Sat |
| 9 | FAM | 3.2 | Low Sat |
| 61 | FAM | 3.2 | Low Sat |
| 15 | FAM | 3.2 | Low Sat |
| 39 | FAM | 3.2 | Low Sat |
| 11 | FAM | 3.2 | Low Sat |
| 53 | FAM | 3.2 | Low Sat |
| 25 | FAM | 3.2 | Low Sat |
| 22 | FAM | 3.2 | Low Sat |
| 65 | FAM | 3.3 | Low Sat |
| 12 | FAM | 3.3 | Low Sat |
| 4 | FAM | 3.3 | Low Sat |
| 50 | FAM | 3.3 | Low Sat |
| 75 | FAM | 3.3 | Low Sat |
| 27 | FAM | 3.4 | Low Sat |
| 42 | FAM | 3.4 | Low Sat |
| 52 | FAM | 3.4 | Low Sat |
| 24 | FAM | 3.4 | Low Sat |
| 70 | FAM | 3.4 | Low Sat |
| 1 | FAM | 3.4 | Low Sat |
| 71 | FAM | 3.5 | Low Sat |
| 58 | FAM | 3.5 | Low Sat |
| 73 | FAM | 3.5 | Low Sat |
| 11 | HET | 3.5 | Low Sat |
| 25 | FAM | 3.5 | Low Sat |
| 12 | FAM | 3.6 | Low Sat |
| 21 | FAM | 3.6 | Low Sat |
| 53 | HET | 3.6 | Low Sat |
| 22 | HET | 3.7 | Low Sat |
| 85 | FAM | 3.7 | Low Sat |
| 68 | VIC | 8.8 | Not Low Sat |
| 36 | VIC | 9.5 | Not Low Sat |
| 77 | VIC | 9.5 | Not Low Sat |
| 61 | HET | 9.6 | Not Low Sat |
| 34 | VIC | 9.6 | Not Low Sat |
| 73 | VIC | 9.7 | Not Low Sat |
| 16 | VIC | 9.7 | Not Low Sat |
| 61 | VIC | 9.7 | Not Low Sat |
| 69 | VIC | 9.7 | Not Low Sat |
| 28 | VIC | 9.7 | Not Low Sat |
| 39 | VIC | 9.7 | Not Low Sat |
| 1 | VIC | 9.8 | Not Low Sat |
| 13 | VIC | 9.9 | Not Low Sat |
| 55 | VIC | 9.9 | Not Low Sat |
| 25 | VIC | 9.9 | Not Low Sat |

Figure 2C

| ID | FAP3_35a_4_1 | R160 | Phenotype |
|---|---|---|---|
| 65 | HET | 10 | Not Low Sat |
| 37 | VIC | 10 | Not Low Sat |
| 76 | VIC | 10 | Not Low Sat |
| 52 | VIC | 10 | Not Low Sat |
| 50 | HET | 10.1 | Not Low Sat |
| 56 | VIC | 10.1 | Not Low Sat |
| 30 | VIC | 10.2 | Not Low Sat |
| 58 | VIC | 10.2 | Not Low Sat |
| 45 | HET | 10.2 | Not Low Sat |
| 73 | VIC | 10.2 | Not Low Sat |
| 27 | VIC | 10.3 | Not Low Sat |
| 82 | VIC | 10.3 | Not Low Sat |
| 2 | HET | 10.5 | Not Low Sat |
| 42 | HET | 10.5 | Not Low Sat |
| 54 | VIC | 10.6 | Not Low Sat |
| 56 | VIC | 10.6 | Not Low Sat |
| 99 | VIC | 10.6 | Not Low Sat |
| 71 | HET | 10.6 | Not Low Sat |
| 16 | VIC | 10.6 | Not Low Sat |
| 36 | VIC | 10.7 | Not Low Sat |
| 3 | HET | 10.8 | Not Low Sat |
| 45 | VIC | 10.9 | Not Low Sat |
| 52 | VIC | 10.9 | Not Low Sat |
| 11 | VIC | 10.9 | Not Low Sat |
| 66 | HET | 11 | Not Low Sat |
| 40 | VIC | 11 | Not Low Sat |
| 56 | HET | 11.1 | Not Low Sat |
| 16 | HET | 11.2 | Not Low Sat |
| 91 | VIC | 11.2 | Not Low Sat |
| 70 | VIC | 11.3 | Not Low Sat |
| 56 | VIC | 11.3 | Not Low Sat |
| 40 | VIC | 11.4 | Not Low Sat |
| 13 | VIC | 11.4 | Not Low Sat |
| 7 | VIC | 11.5 | Not Low Sat |
| 41 | VIC | 11.6 | Not Low Sat |
| 46 | VIC | 11.6 | Not Low Sat |
| 12 | VIC | 11.8 | Not Low Sat |
| 50 | VIC | 11.8 | Not Low Sat |
| 5 | HET | 12 | Not Low Sat |
| 30 | VIC | 12 | Not Low Sat |
| 4 | VIC | 12.1 | Not Low Sat |
| 67 | VIC | 12.3 | Not Low Sat |
| 2 | VIC | 12.6 | Not Low Sat |
| 21 | VIC | 12.6 | Not Low Sat |
| 53 | HET | 12.8 | Not Low Sat |
| 44 | VIC | 12.9 | Not Low Sat |
| 49 | VIC | 12.9 | Not Low Sat |

Figure 4

| Genotype | R160 category |
|---|---|
| 100% favorable | Low Sat |
| 100% non-favorable | Not Low Sat (wildtype value) |
| 28% Het | Low Sat |
| 72% Het | Not Low Sat (wildtype value) |

SOYBEAN SEQUENCES ASSOCIATED WITH THE FAP3 LOCUS

CROSS-REFERENCE TO RELATED APPLICATIONS

This application claims the benefit of U.S. Application Ser. No. 61/332,928 filed May 10, 2010, which is herein incorporated by reference in its entirety.

FIELD OF THE INVENTION

The invention relates to compositions and methods for identifying soybean plants that have lower concentrations of saturated fatty acids. The invention also relates to soybean plants that display lower concentrations of fatty acid that are generated by the methods of the invention.

BACKGROUND

Soybean, a legume, has become the world's primary source of seed oil and seed protein. In addition, its utilization is being expanded to the industrial, manufacturing and pharmaceutical sectors. Soybean productivity is a vital agricultural and economic consideration. Soybean contains saturated fatty acids, such as palmitic and stearic acids. Studies have associated the increased of intake of saturated fatty acids with increased serum cholesterol in the blood. The increased serum cholesterol in turn has been associated with increased risk for coronary heart disease. Decreasing soybean concentrations of saturated fatty acids will make the soybean healthier for the purposes of human consumption as related to coronary heart disease.

Palmitic acid (palmitate) is one of the significant saturated fatty acids found in soybean products. The nomenclature refers to palmitate as 16:0, meaning it is a fatty acid containing 16 carbon atoms and 0 double bonds. The normal value for palmitate is 11% in soybeans. This exceeds the recommended intake. A reduction in saturated fatty acid content will reduce the negative health effects stemming from the high levels of saturated fats found in soybeans.

In soybeans the concentration of saturated fatty acids has been associated with two loci, namely Fap1 and Fap3 where alternative alleles (i.e. non-wild-type) confer phenotypic variation of fatty acid levels in seeds. The Fap3 locus is also known as FatB1 and Fap-nc. Studies have correlated the control and manipulation of particular alleles at these two loci with a decrease in saturated fatty acid content. The description of which allele of Fap 3 (also known as FatB1a or Fap-nc) causes this decrease is a significant advance to generate soybean lines containing lower concentrations of fatty acids.

SUMMARY

A knowledge of which allelic permutation causes this decrease is a significant leap on the path to soybean lines containing lower concentrations of saturated fatty acids. Compositions and methods for identifying such soybean plants with reduced levels of saturated fatty acids are provided. Methods of making soybean plants with reduced levels of saturated fatty acids, e.g., through introgression of desired saturated fatty acid marker alleles and/or by transgenic production methods, as well as plants or germplasm made by these methods, are provided. Systems and kits for selecting plants with reduced levels of saturated fatty acids are also provided.

BRIEF DESCRIPTION OF THE FIGURES

FIG. 2: Table of the allele calls and phenotype for the segregating population for palmitic acid content.

FIG. 4: Tabular representation of the data from FIGS. 2 and 3 to show strong correlation of the homozygosity with the two phenotypic classes.

DETAILED DESCRIPTION

Figure 1:
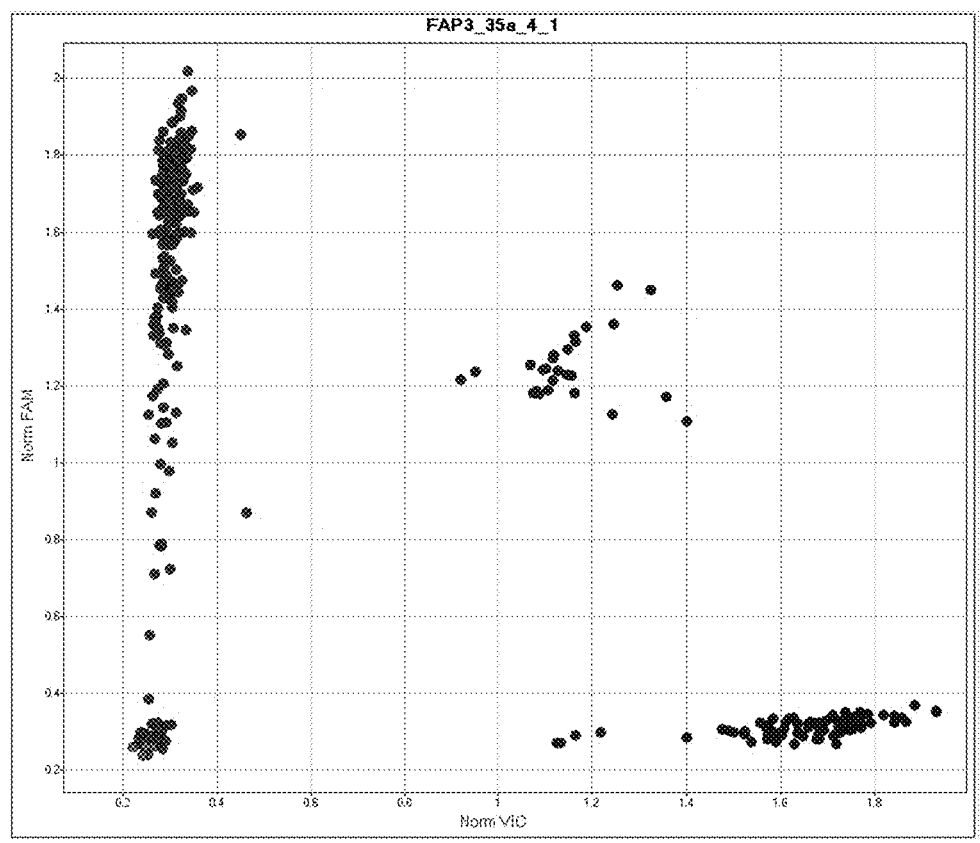
FIG. 1: Scatterplot of a phenotyped population segregating for the Fap3 locus.

While genes affecting soybean saturated fatty acid concentration are known, a method for selecting soybean plants with lower saturated fatty acid concentrations can be time consuming and inaccurate. Finding and selecting a soybean line via marker assisted selection (MAS) at the Fap3 locus is a more efficient and accurate way to generate soybeans with reduced levels of saturated fatty acids than previously used methods. The identification and selection of soybean plants that show reduced levels of fatty acids using MAS can provide an effective and efficient approach to overcoming health concerns caused by increased concentration of saturated fatty acids. The present invention describes a causative SNP in the Fap3 locus that demonstrates statistically significant relation to reduced levels of saturated fatty acids. Detection of this SNP can be used in marker-assisted soybean breeding programs to produce plants with reduced levels of saturated fatty acids.

The Fap3 locus is associated with the FATB1a gene, which is identified as an ACP-thioesterase protein (see, e.g., Cardinal et al. (2007) 47:304-310, and GenBank Accessions DQ861997 and DQ861998). The Fap3 locus has been mapped to soybean linkage group A1 (chromosome 5), within about 2.3 Mb from SATT684. A new allele associated with reduced saturated fatty acid levels was identified in Pioneer soybean line 92B72. The single nucleotide polymorphism (SNP), for example identified at position 62 of SEQ ID NO: 1, provides a predictive allele to identify lines with reduced saturated fatty acids. This SNP position corresponds to position 7995435 in the *Glycine max* genomic reference sequence Glyma 1.0 (www-dot-phytozome-dot-net/soybean; Schmutz et al. (2010) Nature 436:178-183).

Methods for identifying a soybean plant or germplasm (e.g., a line or variety) that has reduced levels of saturated fatty acids are provided. In the methods, at least one novel SNP that is associated with the reduced levels of saturated fatty acids has been detected in the soybean plant or germplasm. The SNP allele is identified by the sequence provided in SEQ ID NO: 1. Studies show that this novel permutation in the region coding for the Fap3 gene directly correlates to reduced levels of saturated fatty acid in the soybean.

The normal value for palmitic acid in soybean is 11%. Methods for identifying soybean varieties with reduced palmitic acid are provided. In the methods, at least one novel SNP that is associated with the reduced levels of palmitic acid has been detected in the soybean plant or germplasm. The low palmitic acid SNP allele is identified by the sequence provided in SEQ ID NO: 1. This novel permutation in the region coding for the Fap3 gene directly correlates to reduced levels of palmitic acid in the soybean (see, e.g., FIG. 2). In some examples, the soybeans comprise 4% or less palmitic acid. In some examples, the palmitic acid level is 3.9%, 3.8%, 3.7%, 3.6%, 3.5%, 3.4%, 3.3%, 3.2%, 3.1%, 3.0%, 2.9%, 2.8%, 2.7%, 2.6%, 2.5%, 2.4%, 2.3%, 2.2%, 2.1%, 2.0%, 1.9%, or lower.

In some examples, the germplasm is a soybean line or variety. In some aspects the reduced levels of saturated fatty acids is a non-race specific reduction in saturated fatty acids. In some aspects, the reduced levels of saturated fatty acids can be quantified using any suitable means, for example, by assaying levels of saturated fatty acids in soybean containing the SNP and those without.

In some examples, the allele that is detected is a favorable allele that correlates with reduced levels of saturated fatty acids. Alternatively, the allele that is detected can be an allele that correlates with wild-type levels of saturated fatty acids, and that allele is counter-selected. For example, alleles that can be selected for (favorable alleles) or against (unfavorable alleles) include those exemplified in SEQ ID NO: 1 or SEQ ID NO: 2 respectively.

It will be appreciated that the ability to identify a SNP marker that correlates with reduced levels of saturated fatty acids provides a method for selecting plants that have the favorable SNP as well. That is, any plant that is identified as comprising a desired SNP (e.g., a SNP that positively correlates reduced levels of saturated fatty acids) can be selected for, while plants that lack the SNP, or that have a SNP that negatively correlates with reduced levels of saturated fatty acids, can be selected against. Thus, in one method, subsequent to identification of a SNP, the methods include selecting (e.g., isolating) the first soybean plant or germplasm, or selecting a progeny of the first plant or germplasm. In some examples, the resulting selected first soybean plant or germplasm can be crossed with a second soybean plant or germplasm (e.g., an elite or exotic soybean, depending on characteristics that are desired in the progeny).

Isolated polynucleotides sequences comprising the SNP and/or used to amplify or detect the SNP associated with reduced saturated fatty acids are provided. In some examples these sequences are amplified sequences, primer sequences, and/or probe sequences. One or more of these sequences, alone or in combination, can be used to detect soybean varieties comprising the polymorphism in Fap3. In some examples, at least one sequence is used to detect the polymorphism on LG A1 that corresponds position 7995435 on chromosome 5 of the *Glycine max* genomic sequence, for example as exemplified at position 62 in SEQ ID NO: 1. In some examples, sequences include SEQ ID NOs: 1-12, as provided in the Sequence Listing. In some examples, the sequences, their derivation, and/or their use is described in the table below. Depending on the detection methodology used, an amplicon sequence may also be used as a probe sequence, e.g., used for hybridization. As illustrated, multiple primer pairs, amplicon, and probe sequences are provided for the detection and/or selection of soybean varieties with reduced saturated fats.

| SEQ ID | Description | SNP position |
|---|---|---|
| 1 | Amplicon of Fap3 locus from Pioneer soybean variety 92B72 comprising the favorable SNP allele | 62 |
| 2 | Amplicon of Fap3 locus from soybean variety Williams82 comprising the wildtype SNP allele | 62 |
| 3 | S04257-1-P1 probe for favorable allele | 8 |
| 4 | S04257-1-P2 probe for wildtype allele | 6 |
| 5 | S04257-1-F1 forward primer | N/A |
| 6 | S04257-1-R1 reverse primer | N/A |

-continued

| SEQ ID | Description | SNP position |
|---|---|---|
| 7 | S04257-1-B amplicon for Fap3 locus | 79 |
| 8 | S04257-1-F3 forward primer | N/A |
| 9 | S04257-1-R3 reverse primer | N/A |
| 10 | S04257-1-C amplicon for Fap3 locus | 79 |
| 11 | S04257-1-F4 forward primer | N/A |
| 12 | S04257-1-R4 reverse primer | N/A |

In some examples, an isolated nucleic acid molecule comprising a nucleotide sequence having a single nucleotide polymorphism correlated with palmitic acid level in soybean is provided. In some examples the nucleotide sequence comprises the sequence set forth in SEQ ID NOs: 1 or 3, comprises a fragment SEQ ID NO:1, wherein said fragment retains the single nucleotide polymorphism and is at least 30, 35, 40, 45, 50, 55, 60, 65, 70, 75, 80, 85, 90, 95, 100, 110, 120, 130, 140, 150, 160, 170, 180, 190, 200, 210, 220, 230, 240, 250, 275, 300, 325, 350, 375, 400, 425, 450, 475, 500, 525, 550, 575, 600, 625, 650, 675, 700, 725, 750, 800, 825, 850, 875, 900, 925, 950, 975, 1000, 1025, 1050, 1075, or 1100 nucleotides in length, or is a sequence fully complementary any one or more of the nucleotide sequences.

Systems for identifying a soybean plant predicted to have reduced levels of saturated fatty acids are also provided. Typically, the systems include: (A) a set of marker primers and/or probes configured to detect at least one favorable allele of one or more marker locus associated with reduced levels of saturated fatty acids, wherein the marker locus or loci are selected from SEQ ID NOs: 1, 2, 7, and/or 10; (B) a detector that is configured to detect one or more signal outputs from the set of marker probes or primers, or amplicon thereof, thereby identifying the presence or absence of the allele; and (C) system instructions that correlate the presence or absence of the favorable allele with the predicted saturated fatty acid content. In some system examples, SNP markers are selected from SEQ ID NOs: 1, 2, 7, or 10. In some examples, the primers are selected from primer pairs of SEQ ID NOs: 5 and 6, 8 and 9, or 11 and 12. In some examples, the marker probes are selected from SEQ ID NOs: 3 and/or 4.

Kits are also provided. For example, a kit can include appropriate primers or probes for detecting reduced fatty acid associated SNP markers and instructions in using the primers or probes for detecting the SNP marker with predicted levels of saturated fatty acids. The kits can further include packaging materials for packaging the probes, primers or instructions, controls such as control amplification reactions that include probes, primers or template nucleic acids for amplifications, molecular size markers, or the like.

In other aspects, nucleic acid compositions that include the novel SNP markers are provided. For example, compositions comprising an amplification primer pair capable of initiating DNA polymerization by a DNA polymerase on a soybean nucleic acid template to generate a soybean marker amplicon, where the marker amplicon corresponds to a soybean marker selected from SEQ ID NOs: 1, 2, 7, or 10 are provided. For example, the primer pair that is specific for the marker can be selected from SEQ ID NOs: 5 and 6, 8 and 9, or 11, and 12. The probe pair that discriminates between the favorable and unfavorable allele can be selected from SEQ ID NOS: 3 and 4 respectively, where the probe of SEQ ID NO:3 can be used to detect to the favorable allele (A and FAM) and the probe of SEQ ID NO:4 can be used to detect to the unfavorable allele (C and VIC).

DEFINITIONS

This invention is not limited to particular embodiments, which can, of course, vary. It is also to be understood that the terminology used herein is for the purpose of describing particular embodiments only, and is not intended to be limiting. As used in this specification and the appended claims, terms in the singular and the singular forms "a," "an" and "the," for example, include plural referents unless the content clearly dictates otherwise. Thus, for example, reference to "plant," "the plant" or "a plant" also includes a plurality of plants; also, depending on the context, use of the term "plant" can also include genetically similar or identical progeny of that plant; use of the term "a nucleic acid" optionally includes, as a practical matter, many copies of that nucleic acid molecule; similarly, the term "probe" optionally (and typically) encompasses many similar or identical probe molecules.

Unless otherwise indicated, nucleic acids are written left to right in 5' to 3' orientation. Numeric ranges recited within the specification are inclusive of the numbers defining the range and include each integer or any non-integer fraction within the defined range. Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, some materials and methods are described herein. In describing and claiming the present invention, the following terminology will be used in accordance with the definitions set out below.

The term ALLELE refers to one of two or more different nucleotide sequences that occur at a specific locus. For example, a first allele can occur on one chromosome, while a second allele occurs on a second homologous chromosome, e.g., as occurs for different chromosomes of a heterozygous individual, or between different homozygous or heterozygous individuals in a population. A "favorable allele" is the allele at a particular locus that confers, or contributes to, a desirable phenotype, e.g., reduced levels of saturated fatty acids. A favorable allele of a marker is a marker allele that segregates with the favorable phenotype. A favorable allelic form is a nucleotide sequence that contributes to a desired characteristic at one or more genetic loci physically located on the chromosome segment. "Allele frequency" refers to the frequency (proportion or percentage) at which an allele is present at a locus within an individual, within a line, or within a population of lines. For example, for an allele "A," diploid individuals of genotype "AA," "Aa," or "aa" have allele frequencies of 1.0, 0.5, or 0.0, respectively. One can estimate the allele frequency within a line by averaging the allele frequencies of a sample of individuals from that line. Similarly, one can calculate the allele frequency within a population of lines by averaging the allele frequencies of lines that make up the population. For a population with a finite number of individuals or lines, an allele frequency can be expressed as a count of individuals or lines (or any other specified grouping) containing the allele.

An ALLELE "POSITIVELY" correlates with a trait when it is linked to it and when presence of the allele is an indictor that the desired trait or trait form will occur in a plant comprising the allele. An allele negatively correlates with a trait when it is linked to it and when presence of the allele is an indicator that a desired trait or trait form will not occur in a plant comprising the allele.

The term AMPLIFYING in the context of nucleic acid amplification is any process whereby additional copies of a selected nucleic acid (or a transcribed form thereof) are produced. Typical amplification methods include various polymerase based replication methods, including the polymerase chain reaction (PCR), ligase mediated methods such as the ligase chain reaction (LCR) and RNA polymerase based amplification (e.g., by transcription) methods. An "amplicon" is an amplified nucleic acid, e.g., a nucleic acid that is produced by amplifying a template nucleic acid by any available amplification method (e.g., PCR, LCR, transcription, or the like).

An individual is HOMOZYGOUS if the individual has only one type of allele at a given locus (e.g., a diploid individual has a copy of the same allele at a locus for each of two homologous chromosomes). An individual is "heterozygous" if more than one allele type is present at a given locus (e.g., a diploid individual with one copy each of two different alleles). The term "homogeneity" indicates that members of a group have the same genotype at one or more specific loci. In contrast, the term "heterogeneity" is used to indicate that individuals within the group differ in genotype at one or more specific loci.

BREEDING means the genetic manipulation of living organisms.

As used herein, the terms CHROMOSOMAL INTERVAL or CHROMOSOME SEGMENT designate a contiguous linear span of genomic DNA that resides in planta on a single chromosome. The genetic elements or genes located on a single chromosome interval are physically linked. The size of a chromosome interval is not particularly limited.

In some aspects, for example, generally the genetic elements located within a single chromosome interval are also genetically linked, typically within a genetic recombination distance of, for example, less than or equal to 20 centimorgan (cM), or alternatively, less than or equal to 10 cM. That is, two genetic elements within a single chromosome interval undergo recombination at a frequency of less than or equal to 20% or 10% respectively.

In one aspect, a marker is linked (genetically and physically) to any other marker that is within 50 cM or less. In another aspect, any marker is closely linked (genetically and physically) to any other marker that is in close proximity, e.g., within 10 cM or less. Two closely linked markers on the same chromosome can be positioned 9, 8, 7, 6, 5, 4, 3, 2, 1, 0.75, 0.5 or 0.25 cM or less from each other.

The term CROSSED or CROSS refers to the fusion of gametes via pollination to produce progeny (e.g., cells, seeds or plants). The term encompasses both sexual crosses (the pollination of one plant by another) and selfing (self-pollination, e.g., when the pollen and ovule are from the same plant).

As used herein, the terms COMPLEMENTARY or COMPLEMENTARITY are used in reference to antiparallel strands of polynucleotides related by the Watson-Crick base-pairing rules. For example, the sequence 5'-AGTTC-3' is complementary to the sequence 5'-GAACT-3'. The terms "completely complementary" or "100% complementary" and the like refer to complementary sequences that have perfect Watson-Crick pairing of bases between the antiparallel strands. The terms "partially complementary," "incomplete complementarity" or "incompletely complementary" and the like refer to any alignment of bases between antiparallel polynucleotide strands that is less than 100% (e.g., has mismatches).

CULTIVAR and VARIETY are used synonymously and mean a group of plants within a species (e.g., *Glycine max*) that share certain genetic traits that separate them from the typical form and from other possible varieties within that species. Soybean cultivars are inbred lines produced after several generations of self-pollinations. Individuals within a soybean cultivar are homogeneous, nearly genetically identical, with most loci in the homozygous state.

GENETIC MARKERS are nucleic acids that are polymorphic in a population and where the alleles of which can be detected and distinguished by one or more analytic methods, e.g., RFLP, AFLP, isozyme, SNP, SSR, and the like. Genetic markers may relate to a genetic locus (a "marker locus") that can be used as a point of reference when identifying a genetically linked or specified target locus such as a QTL. A genetic marker may also refer to an encoded product of a nucleic acid sequence (e.g., a protein) used as a point of reference when identifying a linked locus. A marker can be derived from genomic nucleotide sequence or from expressed nucleotide sequences (e.g., from a spliced RNA, a cDNA, etc.), or from an encoded polypeptide. The term also refers to nucleic acid sequences complementary to or flanking the marker sequences, such as nucleic acids used as probes or primer pairs capable of amplifying the marker sequence. A "marker probe" is a nucleic acid sequence or molecule that can be used to identify the presence of a marker locus, e.g., a nucleic acid probe that is complementary to a marker locus sequence. Alternatively, in some aspects, a marker probe refers to a probe of any type that is able to distinguish (i.e., genotype) the particular allele that is present at a marker locus. A marker probe is typically labeled with any suitable "reporter molecule" so that the probe is detectable. Detection systems include, but are not limited to, the detection of enzymatic activity, fluorescence, radioactivity, luminescence or binding properties that permit specific binding of the reporter (e.g., where the reporter is an antibody). The source of the polynucleotide used in the probe is not limited, and can be produced synthetically, in vitro, or can be a subsequence of a larger nucleic acid molecule isolated from a cell. A PCR primer or PCR primer pair can be a probe for the detection of a target polynucleotide. A "marker allele," alternatively an "allele of a marker locus" is one of a plurality of polymorphic nucleotide sequences found at a marker locus in a population that is polymorphic for the marker locus. Marker loci correlating with reduced saturated fatty acid concentrations in soybean are provided.

Genetic markers corresponding to genetic polymorphisms between members of a population can be detected by methods well-established in the art. These include, e.g., PCR-based sequence specific amplification methods, detection of restriction fragment length polymorphisms (RFLP), detection of isozyme markers, detection of polynucleotide polymorphisms by allele specific hybridization (ASH), detection of amplified variable sequences of the plant genome, detection of self-sustained sequence replication, detection of simple sequence repeats (SSRs), detection of single nucleotide polymorphisms (SNPs), or detection of amplified fragment length polymorphisms (AFLPs). Well-established methods are also known for the detection of expressed sequence tags (ESTs), SSR markers derived from EST sequences, and randomly amplified polymorphic DNA (RAPD). The term also refers to nucleic acid sequences complementary to the marker sequences, such as nucleic acids used as probes.

A GENETIC MAP is a description of genetic linkage relationships among loci on one or more chromosomes (or linkage groups) within a given species, generally depicted in a diagrammatic or tabular form. "Genetic mapping" is the process of defining the linkage relationships of loci through the use of genetic markers, populations segregating for the markers, and standard genetic principles of recombination frequency. A "genetic map location" is a location on a genetic map relative to surrounding genetic markers on the same linkage group where a specified marker can be found within a given species. In contrast, a physical map of the genome refers to absolute distances (for example, measured in base pairs or isolated and overlapping contiguous genetic fragments, e.g., contigs). A physical map of the genome does not take into account the genetic behavior (e.g., recombination frequencies) between different points on the physical map.

The term GENETIC ELEMENT or GENE refers to a heritable sequence of DNA, i.e., a genomic sequence, with functional significance. The term "gene" can also be used to refer to, e.g., a cDNA and/or a mRNA encoded by a genomic sequence, as well as to that genomic sequence.

The term GENOTYPE is the genetic constitution of an individual (or group of individuals) at one or more genetic loci. Genotype is defined by the allele(s) of one or more known loci that the individual has inherited from its parents. The term genotype can be used to refer to an individual's genetic constitution at a single locus, at multiple loci, or, more generally, the term genotype can be used to refer to an individual's genetic make-up for all the nucleic acids in its genome(s). A "haplotype" is the genotype of an individual at a plurality of genetic loci. Typically, the genetic loci described by a haplotype are physically and genetically linked, i.e., on the same chromosome segment.

A GENETIC RECOMBINATION FREQUENCY or GENETIC DISTANCE is the frequency of a crossing over event (recombination) between two genetic loci. Recombination frequency can be observed by following the segregation of markers and/or traits following meiosis. A genetic recombination frequency can be expressed in centimorgans (cM), where one cM is the distance between two genetic markers that show a 1% recombination frequency (i.e., a crossing-over event occurs between those two markers once in every 100 cell divisions).

A GENOMIC NUCLEIC ACID or GENOMIC SEQUENCE is a nucleic acid that corresponds in sequence to a heritable nucleic acid in a cell. Common examples include nuclear genomic DNA and amplicons thereof. A genomic nucleic acid is, in some cases, different from a spliced RNA, or a cDNA, in that the spliced RNA or cDNA is processed, to remove introns. Genomic nucleic acids optionally comprise non-transcribed (e.g., chromosome structural sequences, promoter regions, enhancer regions, etc.) and/or non-translated sequences (e.g., introns), whereas spliced RNA/cDNA typically do not have non-transcribed sequences or introns. A "template nucleic acid" is a nucleic acid that serves as a template in an amplification reaction (e.g., a polymerase based amplification reaction such as PCR, a ligase mediated amplification reaction such as LCR, a transcription reaction, or the like). A template nucleic acid can be genomic in origin, or alternatively, can be derived from expressed sequences, e.g., an RNA, a cDNA, or an EST.

An EXOGENOUS NUCLEIC ACID is a nucleic acid that is not native to a specified system (e.g., a germplasm, plant, variety, etc.), with respect to sequence, genomic position, or both. As used herein, the terms "exogenous" or "heterologous" as applied to polynucleotides or polypeptides typically refers to molecules that have been artificially supplied to a biological system (e.g., a plant cell, a plant gene, a particular plant species or variety or a plant chromosome under study) and are not native to that particular biological system. The terms can indicate that the relevant material originated from a source other than a naturally occurring source, or can refer to molecules having a non-natural configuration, genetic location or arrangement of parts.

A NATIVE or ENDOGENOUS nucleic acid is a polynucleotide that does not contain nucleic acid elements encoded by sources other than the chromosome or other genetic element on which it is normally found in nature. An endogenous nucleic acid, transcript or polypeptide is encoded by its natural chromosomal locus, and not artificially supplied to the cell.

The term RECOMBINANT in reference to a nucleic acid or polypeptide indicates that the material (e.g., a recombinant nucleic acid, gene, polynucleotide, polypeptide, etc.) has been altered by human intervention. Generally, the arrangement of parts of a recombinant molecule is not a native configuration, or the primary sequence of the recombinant polynucleotide or polypeptide has in some way been manipulated. The alteration to yield the recombinant material can be performed on the material within or removed from its natural environment or state. For example, a naturally occurring nucleic acid becomes a recombinant nucleic acid if it is altered, or if it is transcribed from DNA which has been altered, by means of human intervention performed within the cell from which it originates.

GERMPLASM refers to genetic material of or from an individual (e.g., a plant), a group of individuals (e.g., a plant line, variety or family), or a clone derived from a line, variety, species, or culture. The germplasm can be part of an organism or cell, or can be separate from the organism or cell. In general, germplasm provides genetic material with a specific molecular makeup that provides a physical foundation for some or all of the hereditary qualities of an organism or cell culture. As used herein, germplasm includes cells, seed or tissues from which new plants may be grown, or plant parts, such as leafs, stems, pollen, or cells, which can be cultured into a whole plant.

The term INTROGRESSION refers to the transmission of a desired allele of a genetic locus from one genetic background to another. For example, introgression of a desired allele at a specified locus can be transmitted to at least one progeny via a sexual cross between two parents of the same species, where at least one of the parents has the desired allele in its genome. Alternatively, for example, transmission of an allele can occur by recombination between two donor genomes, e.g., in a fused protoplast, where at least one of the donor protoplasts has the desired allele in its genome. The desired allele can be, e.g., a selected allele of a marker, a QTL, a transgene, or the like. In any case, offspring comprising the desired allele can be repeatedly backcrossed to a line having a desired genetic background and selected for the desired allele, to result in the allele becoming fixed in a selected genetic background.

A LINE or STRAIN is a group of individuals of identical parentage that are generally inbred to some degree and that are generally homozygous and homogeneous at most loci (isogenic or near isogenic). A "subline" refers to an inbred subset of descendents that are genetically distinct from other similarly inbred subsets descended from the same progenitor. Traditionally, a "subline" has been derived by inbreeding the seed from an individual soybean plant selected at the $F_3$ to $F_5$ generation until the residual segregating loci are "fixed" or homozygous across most or all loci. Commercial soybean varieties (or lines) are typically produced by aggregating ("bulking") the self-pollinated progeny of a single $F_3$ to $F_5$ plant from a controlled cross between 2 genetically different parents. While the variety typically appears uniform, the self-pollinating variety derived from the selected plant eventually (e.g., $F_8$) becomes a mixture of homozygous plants that can vary in genotype at any locus that was heterozygous in the originally selected $F_3$ to $F_5$ plant. Marker-based sublines, that differ from each other based on qualitative polymorphism at the DNA level at one or more specific marker loci, are derived by genotyping a sample of seed derived from individual self-pollinated progeny derived from a selected $F_3$-$F_5$ plant. The seed sample can be genotyped directly as seed, or as plant tissue grown from such a seed sample. Optionally, seed sharing a common genotype at the specified locus (or loci) are bulked providing a subline that is genetically homogenous at identified loci important for a trait of interest (yield, level of saturated fatty acid, etc.).

An ANCESTRAL LINE is a parent line used as a source of genes e.g., for the development of elite lines. An "ancestral population" is a group of ancestors that have contributed the bulk of the genetic variation that was used to develop elite lines. "Descendants" are the progeny of ancestors, and may be separated from their ancestors by many generations of breeding. For example, elite lines are the descendants of their ancestors. A "pedigree structure" defines the relationship between a descendant and each ancestor that gave rise to that descendant. A pedigree structure can span one or more generations, describing relationships between the descendant and its parents, grandparents, great-grandparents, etc.

An ELITE LINE or ELITE STRAIN is an agronomically superior line that has resulted from many cycles of breeding and selection for superior agronomic performance. Numerous elite lines are available and known to those of skill in the art of soybean breeding. An "elite population" is an assortment of elite individuals or lines that can be used to represent the state of the art in terms of agronomically superior genotypes of a given crop species, such as soybean. Similarly, an "elite germplasm" or elite strain of germplasm is an agronomically superior germplasm, typically derived from and/or capable of giving rise to a plant with superior agronomic performance, such as an existing or newly developed elite line of soybean.

In contrast, an EXOTIC SOYBEAN STRAIN or an EXOTIC SOYBEAN GERMPLASM is a strain or germplasm derived from a soybean not belonging to an available elite soybean line or strain of germplasm. In the context of a cross between two soybean plants or strains of germplasm, an exotic germplasm is not closely related by descent to the elite germplasm with which it is crossed. Most commonly, the exotic germplasm is not derived from any known elite line of soybean, but rather is selected to introduce novel genetic elements (typically novel alleles) into a breeding program.

As used herein, the term LINKAGE is used to describe the degree to which one marker locus is associated with another marker locus or some other locus.

As used herein, LINKAGE EQUILIBRIUM describes a situation where two markers independently segregate, i.e., sort among progeny randomly. Markers that show linkage equilibrium are considered unlinked (whether or not they lie on the same chromosome).

As used herein, LINKAGE DISEQUILIBRIUM describes a situation where two markers segregate in a non-random manner, i.e., have a recombination frequency of less than 50% (and by definition, are separated by less than 50 cM on the same linkage group). Markers that show linkage disequilibrium are considered linked. Linkage occurs when the marker locus and a linked locus are found together in progeny plants more frequently than not together in the progeny plants. As used herein, linkage can be between two markers, or alternatively between a marker and a phenotype. The degree of linkage of a molecular marker to a phenotypic trait (e.g., a QTL) is measured, e.g., as a statistical probability of co-segregation of that molecular marker with the phenotype.

As used herein, the linkage relationship between a molecular marker and a phenotype is given as a PROBABILITY or ADJUSTED PROBABILITY. The probability value is the statistical likelihood that the particular combination of a phenotype and the presence or absence of a particular marker allele is random. Thus, the lower the probability score, the greater the likelihood that a phenotype and a particular marker will co-segregate. In some aspects, the probability score is considered "significant" or "nonsignificant." In some examples, a probability score of 0.05 (p=0.05, or a 5% probability) of random assortment is considered a significant indication of co-segregation. An acceptable probability can be any probability of less than 50% (p=0.5). For example, a significant probability can be less than 0.25, less than 0.20, less than 0.15, or less than 0.1.

Advantageously, the two linked loci are located in close proximity such that recombination between homologous chromosome pairs does not occur between the two loci during meiosis with high frequency, e.g., such that linked loci co-segregate at least about 90% of the time, e.g., 91%, 92%, 93%, 94%, 95%, 96%, 97%, 98%, 99%, 99.5%, 99.75%, or more of the time.

A LOCUS is a chromosomal region where a polymorphic nucleic acid, trait determinant, gene or marker is located. Thus, for example, a "gene locus" is a specific chromosome location in the genome of a species where a specific gene can be found.

The term QUANTITATIVE TRAIT LOCUS (QTL) refers to a polymorphic genetic locus with at least two alleles that differentially affect the expression of a phenotypic trait in at least one genetic background, e.g., in at least one breeding population. A QTL may act through a single gene or by a polygenic mechanism.

MARKER ASSISTED SELECTION refers to the process of selecting a desired trait or desired traits in a plant or plants by detecting one or more genetic markers from the plant, where the genetic marker is linked to the desired trait.

POLYMERASE CHAIN REACTION (PCR) refers to a well known method using primer-based amplification of template nucleic acids to increase the concentration of a segment of a target polynucleotide in a sample, where the sample can be a single polynucleotide species, or multiple polynucleotides. Reverse transcriptase PCR (RT-PCR) is a PCR reaction that uses RNA template and a reverse transcriptase to first generate a single stranded DNA molecule prior to the multiple cycles of DNA-dependent DNA polymerase primer elongation. Multiplex PCR refers to PCR reactions that produce more than one amplified product in a single reaction, typically by the inclusion of more than two primers in a single reaction. Methods for a wide variety of PCR applications are widely known in the art, and described in many sources, for example, Ausubel et al. (eds.), Current Protocols in Molecular Biology, Section 15, John Wiley & Sons, Inc., New York (1994).

The terms PHENOTYPE, or PHENOTYPIC TRAIT, or TRAIT refers to one or more traits of an organism. The phenotype can be observable to the naked eye, or by any other means of evaluation known in the art, including but not limited to microscopy, biochemical analysis, genomic analysis, positive selection, assays, molecular characterization, marker analysis, PCR, protein analysis, insect resistance, herbicide resistance, morphology, disease resistance, sequencing, and the like. In some cases, a phenotype is directly controlled by a single gene or genetic locus, i.e., a "single gene trait." In other cases, a phenotype is the result of several genes.

A MOLECULAR PHENOTYPE is a phenotype detectable at the level of a population of (one or more) molecules. Such molecules can be nucleic acids such as genomic DNA or RNA, proteins, or metabolites. For example, a molecular phenotype can be an expression profile for one or more gene products, e.g., at a specific stage of plant development, in response to an environmental condition or stress, etc. Expression profiles are typically evaluated at the level of RNA or protein, e.g., on a nucleic acid array or "chip" or using antibodies or other binding proteins.

As used herein, it is not intended that the term POLYNUCLEOTIDES be limited to naturally occurring polynucleotides, naturally occurring backbones or naturally occurring internucleotide linkages. One familiar with the art knows well the wide variety of polynucleotide analogues, unnatural nucleotides, non-natural phosphodiester bond linkages and internucleotide analogs. Non-limiting examples of such unnatural structures include non-ribose sugar backbones, 3'-5' and 2'-5' phosphodiester linkages, internucleotide inverted linkages (e.g., 3'-3' and 5'-5'), branched structures, and internucleotide analogs (e.g., peptide nucleic acids (PNAs), locked nucleic acids (LNAs), CI-C4 alkylphosphonate linkages such as methylphosphonate, phosphoramidate, CI-Cs alkyl-phosphotriester, phosphorothioate and phosphorodithioate internucleotide linkages. Furthermore, a polynucleotide may be composed entirely of a single type of monomeric subunit and one type of linkage, or can be composed of mixtures or combinations of different types of subunits and different types of linkages (a polynucleotide can be a chimeric molecule). As used herein, a polynucleotide analog retains the essential nature of natural polynucleotides in that it hybridizes to a single-stranded nucleic acid target in a manner similar to naturally occurring polynucleotides.

A PLANT can be a whole plant, any part thereof, or a cell or tissue culture derived from a plant. Thus, plant can refer to any of: whole plants, plant components or organs (e.g., leaves, stems, roots, etc.), plant tissues, seeds, plant cells, and/or progeny of the same. A plant cell is a cell of a plant, taken from a plant, or derived through culture from a cell taken from a plant. Soybean plant includes whole soybean plants, soybean plant cells, soybean protoplasts, soybean tissue or cell culture from which soybean plants can be regenerated, soybean plant calli, soybean plant clumps, and soybean plant cells that are intact in soybean plants or parts of soybean plants, such as soybean seeds, soybean pods, soybean flowers, soybean cotyledons, soybean leaves, soybean stems, soybean buds, soybean roots, soybean root tips and the like.

POSITIONAL CLONING is a procedure in which a target nucleic acid is identified and isolated by its genomic proximity to marker nucleic acid. For example, a genomic nucleic acid clone can include part or all of two more chromosomal regions that are proximal to one another. If a marker can be used to identify the genomic nucleic acid clone from a genomic library, standard methods such as sub-cloning or sequencing can be used to identify and or isolate subsequences of the clone that are located near the marker.

A SET of markers or probes refers to a collection or group of markers or probes, or the data derived therefrom, used for a common purpose, e.g., identifying soybean plants with a desired trait (e.g., reduced levels of saturated fatty acids). Frequently, data corresponding to the markers or probes, or data derived from their use, is stored in an electronic medium. While each of the members of a set possess utility with respect to the specified purpose, individual markers selected from the set as well as subsets including some, but not all of the markers, are also effective in achieving the specified purpose.

SNP means single nucleotide polymorphism. SNPs are genetic markers in which DNA sequence variations that occur when a single nucleotide (A, T, C, or G) in the genome sequence is altered are mapped to sites on the soybean genome. Many techniques for detecting SNPs are known in the art, including allele specific hybridization, primer extension, and direct sequencing.

SPECIFIC HYBRIDIZATION means binding, duplexing, or hybridizing of a molecule only to a particular nucleotide sequence under stringent conditions such that the probe will hybridize to its target subsequence, but not to other sequences. Stringent conditions are sequence-dependent and are different in different circumstances. Longer sequences hybridize specifically at higher temperatures. Generally, stringent conditions are selected to be about 5° C. lower than the thermal melting point (Tm) for the specific sequence at a defined ionic strength and pH. The Tm is the temperature (under defined ionic strength, pH, and nucleic acid concentration) at which 50% of the probes complementary to the target sequence hybridize to the target sequence at equilibrium. Typically, stringent conditions include a salt concentration of at least about 0.01 to 1.0 M Na ion concentration (or other salts) at pH 7.0 to 8.3 and the temperature is at least about 30° C. for short probes (e.g., 10 to 50 nucleotides). Stringent conditions can also be achieved with the addition of destabilizing agents such as formamide. For example, conditions of 5×SSPE (750 mM NaCl, 50 mM NaPhosphate, 5 mM EDTA, pH 7.4) and a temperature of 25°-30° C. are suitable for allele-specific probe hybridizations. A perfectly matched probe has a sequence perfectly complementary to a particular target sequence (U.S. Pat. No. 6,368,799).

TRANSGENIC is used herein to refer to any cell, cell line, callus, tissue, plant part or plant, the genotype of which has been altered by the presence of heterologous nucleic acid including those transgenic organisms or cells initially so altered, as well as those created by crosses or asexual propagation from the initial transgenic organism or cell. The term "transgenic" as used herein does not encompass the alteration of the genome (chromosomal or extra-chromosomal) by conventional plant breeding methods (e.g., crosses) or by naturally occurring events such as random cross-fertilization, non-recombinant viral infection, non-recombinant bacterial transformation, non-recombinant transposition, or spontaneous mutation.

The term YIELD refers to the productivity per unit area of a particular plant product of commercial value. For example, yield of soybean is commonly measured in bushels of seed per acre or metric tons of seed per hectare per season. Yield is affected by both genetic and environmental factors. "Agronomics," "agronomic traits," and "agronomic performance" refer to the traits (and underlying genetic elements) of a given plant variety that contribute to yield over the course of growing season. Individual agronomic traits include emergence vigor, vegetative vigor, stress tolerance, disease resistance or tolerance, herbicide resistance, branching, flowering, seed set, seed size, seed density, standability, threshability and the like. Yield is, therefore, the final culmination of all agronomic traits.

The development of molecular genetic markers has facilitated mapping and selection of agriculturally important traits in soybean. Markers tightly linked to lower concentrations of saturated fatty acid genes are an asset in the rapid identification of healthier soybean lines on the basis of genotype by the use of marker assisted selection (MAS). Introgressing lower saturated fatty acid genes into a desired cultivar would also be facilitated by using suitable DNA markers.

Molecular Markers and Marker Assisted Selection

A genetic map is a graphical representation of a genome (or a portion of a genome such as a single chromosome) where the distances between landmarks on the chromosome are measured by the recombination frequencies between the landmarks. A genetic landmark can be any of a variety of known polymorphic markers, for example but not limited to, molecular markers such as SSR markers, RFLP markers, or SNP markers. Furthermore, SSR markers can be derived from genomic or expressed nucleic acids (e.g., ESTs). The nature of these physical landmarks and the methods used to detect them vary, but all of these markers are physically distinguishable from each other (as well as from the plurality of alleles of any one particular marker) on the basis of polynucleotide length and/or sequence.

Although specific DNA sequences which encode proteins are generally well-conserved across a species, other regions of DNA (typically non-coding) tend to accumulate polymorphisms, and therefore, can be variable between individuals of the same species. Such regions provide the basis for numerous molecular genetic markers. In general, any differentially inherited polymorphic trait (including nucleic acid polymorphism) that segregates among progeny is a potential marker. The genomic variability can be of any origin, for example, insertions, deletions, duplications, repetitive elements, point mutations, recombination events, or the presence and sequence of transposable elements. A large number of soybean molecular markers are known in the art, and are published or available from various sources, such as the SOYBASE internet resource. Similarly, numerous methods for detecting molecular markers are also well-established.

Molecular marker technologies provide means to increase breeding efficiency through marker assisted selection (MAS). A molecular marker allele that demonstrates linkage disequilibrium with a desired phenotypic trait (e.g., a quantitative trait locus, or QTL, such as resistance to a particular disease) provides a useful tool for the selection of a desired trait in a plant population. The key components to the implementation of this approach are: (i) the creation of a genetic map of molecular markers, (ii) the detection of QTL based on statistical associations between marker and phenotypic variability, (iii) the definition of a set of desirable marker alleles based on the results of the QTL analysis, and (iv) the use and/or extrapolation of this information to the current set of breeding germplasm to enable marker-based selection decisions to be made.

The availability of integrated linkage maps of the soybean genome containing increasing densities of public soybean markers has facilitated soybean genetic mapping and MAS. See, e.g., Cregan et al. (1999) "An Integrated Genetic Linkage Map of the Soybean Genome" Crop Sci. 39:1464-1490; Song et al., "A New Integrated Genetic Linkage Map of the Soybean," Theor. Appl. Genet. 109:122-128 (2004); Diwan and Cregan (1997) "Automated sizing of fluorescent-labeled simple sequence repeat (SSR) markers to assay genetic variation in Soybean," Theor. Appl. Genet. 95:220-225; the Soybase resources on the world wide web at soybase.org, including the Shoemaker Lab Home Page and other resources that can be accessed through Soybase; and see the Soybean Genomics and Improvements Laboratory (SGIL) on the world wide web, and see especially the Cregan Lab web site.

Two types of markers are frequently used in marker assisted selection protocols, simple sequence repeat (SSR, also known as microsatellite) markers, and single nucleotide polymorphism (SNP) markers. The term SSR refers generally to any type of molecular heterogeneity that results in length variability, and most typically is a short (up to several hundred base pairs) segment of DNA that consists of multiple tandem repeats of a two or three base-pair sequence. These repeated sequences result in highly polymorphic DNA regions of variable length due to poor replication fidelity, e.g., caused by polymerase slippage. SSRs appear to be randomly dispersed through the genome and are generally flanked by conserved regions. SSR markers can also be derived from RNA sequences (in the form of a cDNA, a partial cDNA or an EST) as well as genomic material.

The characteristics of SSR heterogeneity make them well suited for use as molecular genetic markers; namely, SSR genomic variability is inherited, is multiallelic, codominant and is reproducibly detectable. The proliferation of increasingly sophisticated amplification-based detection techniques (e.g., PCR-based) provides a variety of sensitive methods for the detection of nucleotide sequence heterogeneity. Primers (or other types of probes) are designed to hybridize to conserved regions that flank the SSR domain, resulting in the amplification of the variable SSR region. The different sized amplicons generated from an SSR region have characteristic and reproducible sizes. The different sized SSR amplicons observed from two homologous chromosomes in an individual, or from different individuals in the plant population are generally termed marker alleles. As long as there are at least two SSR alleles that produce PCR products with at least two different sizes, the SSRs can be employed as markers.

Soybean markers that rely on single nucleotide polymorphisms (SNPs) are also well known in the art. Single nucleotide polymorphisms (SNP) are markers that consist of a shared sequence differentiated on the basis of a single nucleotide. Typically, this distinction is detected by differential migration patterns of an amplicon comprising the SNP on e.g., an acrylamide gel. However, alternative modes of detection, such as hybridization, e.g., ASH, or RFLP analysis are also appropriate. Various techniques have been developed for the detection of SNPs, including allele specific hybridization (ASH; see, e.g., Coryell et al. (1999) "Allele specific hybridization markers for soybean," Theor. Appl. Genet. 98:690-696). Additional types of molecular markers are also widely used, including but not limited to expressed sequence tags (ESTs), SSR markers derived from EST sequences, restriction fragment length polymorphism (RFLP), amplified fragment length polymorphism (AFLP), randomly amplified polymorphic DNA (RAPD) and isozyme markers. A wide range of protocols are known to one of skill in the art for detecting this variability, and these protocols are frequently specific for the type of polymorphism they are designed to detect. For example, PCR amplification, single-strand conformation polymorphisms (SSCP) and self-sustained sequence replication (3SR; see Chan and Fox (1999) "NASBA and other transcription-based amplification methods for research and diagnostic microbiology," Rev Med Microbiol 10:185-196).

Linkage of one molecular marker to another molecular marker is measured as a recombination frequency. In general, the closer two loci (e.g., two SSR markers) are on the genetic map, the closer they lie to each other on the physical map. A relative genetic distance is generally proportional to the physical distance (measured in base pairs, e.g., kilobase pairs [kb] or megabasepairs [Mbp]) between two linked loci on a chromosome. A lack of precise proportionality between cM and physical distance can result from variation in recombination frequencies for different chromosomal regions. In general, the closer one marker is to another marker, whether measured in terms of recombination or physical distance, the more strongly they are linked. In some aspects, the closer a molecular marker is to a gene that encodes a polypeptide that imparts a particular phenotype (reduced levels of saturated fatty acids), whether measured in terms of recombination or physical distance, the better that marker serves to identify the desired phenotypic trait.

Genetic mapping variability can also be observed between different populations of the same crop species, including soybean. In spite of this variability in the genetic map that may occur between populations, genetic map and marker information derived from one population generally remains useful across multiple populations in identification of plants with desired traits, counter-selection of plants with undesirable traits and in guiding MAS.

A method for determining alleles of the FATB1a gene (see, for example GenBank Accessions DQ861997 and DQ861998, and proteins encoded thereby) which affects levels of saturated fatty acids in soybean is disclosed. In accordance with this method, a sample of nucleic acids from a soybean is assayed for the nucleotides at the SNP in the FATB1a. The SNP is located, for example, at position 62 of SEQ ID NO: 1.

The allele predictive of palmitic acid levels comprises a polymorphism at position 62 in SEQ ID NO: 1, where the nucleotide is A is predictive (in the homozygous state) of an individual with reduced levels of palmitic acid (SEQ ID NO: 1). When the nucleotide is C at position 62 (SEQ ID NO: 2) (in the homozygous state) wild type levels of palmitic acid are expected.

The SNP in the Fap3 gene may be used as a marker for identifying soybean with reduced levels of saturated fatty acids. The SNP also may be used as a marker to select for soybean having the alleles associated with reduced levels of saturated fatty acids for use in breeding programs to produce progeny which will also yield soybean with reduced saturated fatty acids. Soybeans identified as comprising the SNP would be retained for breeding. Soybeans comprising the SNP associated with wild-type levels of saturated fatty acids would normally not be selected for breeding. The methods and compositions may be practiced with any legume, as has been exemplified in soybean.

Techniques for Marker Detection

Molecular markers that identify a SNP associated with reduced levels of saturated fatty acids are provided. These SNP markers find use in marker assisted selection for desired traits (reduced levels of saturated fatty acids), and also have other uses. Any method or combination of methods for the detection of these markers can be used.

Markers corresponding to genetic polymorphisms between members of a population can be detected by numerous methods well-established in the art (e.g., PCR-based sequence specific amplification, restriction fragment length polymorphisms (RFLPs), isozyme markers, allele specific hybridization (ASH), amplified variable sequences of the plant genome, self-sustained sequence replication, simple sequence repeat (SSR), single nucleotide polymorphism (SNP), random amplified polymorphic DNA (RAPD) or amplified fragment length polymorphisms (AFLP). In one additional example, the presence or absence of a molecular marker is determined simply through nucleotide sequencing of the polymorphic marker region. This method is readily adapted to high throughput analysis as are the other methods noted above, e.g., using available high throughput sequencing methods such as sequencing by hybridization.

In general, the majority of genetic markers rely on one or more property of nucleic acids for their detection. For example, some techniques for detecting genetic markers utilize hybridization of a probe nucleic acid to nucleic acids corresponding to the genetic marker (e.g., amplified nucleic acids produced using genomic soybean DNA as a template). Hybridization formats, including but not limited to solution phase, solid phase, mixed phase, or in situ hybridization assays are useful for allele detection. An extensive guide to the hybridization of nucleic acids is found in Tijssen (1993) *Laboratory Techniques in Biochemistry and Molecular Biology—Hybridization with Nucleic Acid Probes* Elsevier, New York.

Nucleic acid probes to the marker loci can be cloned and/or synthesized. Any suitable label can be used with a probe. Detectable labels suitable for use with nucleic acid probes include, for example, any composition detectable by spectroscopic, radioisotopic, photochemical, biochemical, immunochemical, electrical, optical or chemical means. Useful labels include biotin for staining with labeled streptavidin conjugate, magnetic beads, fluorescent dyes, radiolabels, enzymes, and colorimetric labels. Other labels include ligands which bind to antibodies labeled with fluorophores, chemiluminescent agents, and enzymes. A probe can also constitute radiolabelled PCR primers that are used to generate a radiolabelled amplicon. Labeling strategies for labeling nucleic acids and corresponding detection strategies can be found, e.g., in Haugland (1996) *Handbook of Fluorescent Probes and Research Chemicals Sixth Edition* by Molecular Probes, Inc. (Eugene Oreg.); or Haugland (2001) *Handbook of Fluorescent Probes and Research Chemicals Eighth Edition* by Molecular Probes, Inc. (Eugene Oreg.).

PCR, RT-PCR and LCR are common methods for amplifying nucleic acids of interest (e.g., those comprising marker loci), and facilitating detection of the markers. Many available biology texts also have extended discussions regarding PCR and related amplification methods. One of skill will appreciate that essentially any RNA can be converted into a double stranded DNA suitable for restriction digestion, PCR expansion and sequencing using reverse transcriptase and a polymerase ("Reverse Transcription-PCR, or "RT-PCR").

In one aspect, real time PCR or LCR is performed on amplification mixtures, e.g., using molecular beacons or TaqMan™ probes. A molecular beacon (MB) is an oligonucleotide or PNA which, under appropriate hybridization conditions, self-hybridizes to form a stem and loop structure. The MB has a label and a quencher at the termini of the oligonucleotide or PNA; thus, under conditions that permit intramolecular hybridization, the label is typically quenched (or at least altered in its fluorescence) by the quencher. Under conditions where the MB does not display intra-molecular hybridization (e.g., when bound to a target nucleic acid, e.g., to a region of an amplicon during amplification), the MB label is unquenched. Details regarding standard methods of making and using MBs are well established in the literature and MBs are available from a number of commercial reagent sources. See, e.g., Leone et al. (1995) "Molecular beacon probes combined with amplification by NASBA enable homogenous real-time detection of RNA." Nucl Acids Res. 26:2150-2155; Tyagi and Kramer (1996) "Molecular beacons: probes that fluoresce upon hybridization" Nat Biotechnol 14:303-308; Blok and Kramer (1997) "Amplifiable hybridization probes containing a molecular switch" Mol Cell Probes 11:187-194; Hsuih et al. (1997) "Novel, ligation-dependent PCR assay for detection of hepatitis C in serum" J Clin Microbiol 34:501-507; Kostrikis et al. (1998) "Molecular beacons: spectral genotyping of human alleles" Science 279:1228-1229; Sokol et al. (1998) "Real time detection of DNA:RNA hybridization in living cells" Proc. Natl. Acad. Sci. U.S.A. 95:11538-11543; Tyagi et al. (1998) "Multicolor molecular beacons for allele discrimination" Nat Biotechnol 16:49-53; Bonnet et al. (1999) "Thermodynamic basis of the chemical specificity of structured DNA probes" Proc. Natl. Acad. Sci. U.S.A. 96:6171-6176; Fang et al. (1999) "Designing a novel molecular beacon for surface-immobilized DNA hybridization studies" J. Am. Chem. Soc. 121:2921-2922; Marras et al. (1999) "Multiplex detection of single-nucleotide variation using molecular beacons" Genet. Anal. Biomol. Eng. 14:151-156; and Vet et al. (1999) "Multiplex detection of four pathogenic retroviruses using molecular beacons" Proc. Natl. Acad. Sci. U.S.A. 96:6394-6399. Additional details regarding MB construction and use is found in the patent literature, e.g., U.S. Pat. Nos. 5,925,517, 6,150,097, and 6,037,130.

PCR detection and quantification using dual-labeled fluorogenic oligonucleotide probes, commonly referred to as "TaqMan™" probes, can also be performed. These probes are composed of short (e.g., 13-20 bases in length) oligonucleotides that are labeled with two different fluorescent dyes. On the 5' terminus of each probe is a reporter dye, and on the 3' terminus of each probe a quenching dye is found. The oligonucleotide probe sequence is complementary to an internal target sequence present in a PCR amplicon. When the probe is intact, energy transfer occurs between the two fluorophores and emission from the reporter is quenched by the quencher by FRET. During the extension phase of PCR, the probe is cleaved by 5' exonuclease activity of the polymerase used in the reaction, thereby releasing the reporter from the oligonucleotide-quencher and producing an increase in reporter emission intensity. Accordingly, TaqMan™ probes are oligonucleotides that have a label and a quencher, where the label is released during amplification by the exonuclease action of the polymerase used in amplification. This provides a real time measure of amplification during synthesis. A variety of TaqMan™ reagents are commercially available, e.g., from Applied Biosystems (Division Headquarters in Foster City, Calif.) as well as from a variety of specialty vendors such as Biosearch Technologies (e.g., black hole quencher probes).

Amplified variable sequences refer to amplified sequences of the plant genome which exhibit high nucleic acid residue variability between members of the same species. All organisms have variable genomic sequences and each organism (with the exception of a clone) has a different set of variable sequences. Once identified, the presence of specific variable sequence can be used to predict phenotypic traits. Typically, DNA from the plant serves as a template for amplification with primers that flank a variable sequence of DNA. The variable sequence is amplified and then sequenced.

Alternatively, self-sustained sequence replication can be used to identify genetic markers. Self-sustained sequence replication refers to a method of nucleic acid amplification using target nucleic acid sequences which are replicated exponentially in vitro under substantially isothermal conditions by using three enzymatic activities involved in retroviral replication: (1) reverse transcriptase, (2) RNase H, and (3) a DNA-dependent RNA polymerase. By mimicking the retroviral strategy of RNA replication by means of cDNA intermediates, this reaction accumulates cDNA and RNA copies of the original target.

Amplified fragment length polymorphisms (AFLP) can also be used as genetic markers. Amplified fragment length polymorphism refers to selected restriction fragments which are amplified before or after cleavage by a restriction endonuclease. The amplification step allows easier detection of specific restriction fragments. AFLP allows the detection large numbers of polymorphic markers and has been used for genetic mapping of plants.

Allele-specific hybridization (ASH) can be used to identify the genetic markers of the invention. ASH technology is based on the stable annealing of a short, single-stranded, oligonucleotide probe to a completely complementary single-strand target nucleic acid. Detection is via an isotopic or non-isotopic label attached to the probe.

For each polymorphism, two or more different ASH probes are designed to have identical DNA sequences except at the polymorphic nucleotides. Each probe will have exact homology with one allele sequence so that the range of probes can distinguish all the known alternative allele sequences. Each probe is hybridized to the target DNA. With appropriate probe design and hybridization conditions, a single-base mismatch between the probe and target DNA will prevent hybridization. In this manner, only one of the alternative probes will hybridize to a target sample that is homozygous or homogenous for an allele. Samples that are heterozygous or heterogeneous for two alleles will hybridize to both of two alternative probes.

ASH markers are used as dominant markers where the presence or absence of only one allele is determined from hybridization or lack of hybridization by only one probe. The alternative allele may be inferred from the lack of hybridization. ASH probe and target molecules are optionally RNA or DNA; the target molecules are any length of nucleotides beyond the sequence that is complementary to the probe; the probe is designed to hybridize with either strand of a DNA target; the probe ranges in size to conform to variously stringent hybridization conditions, etc.

PCR allows the target sequence for ASH to be amplified from low concentrations of nucleic acid in relatively small volumes. Otherwise, the target sequence from genomic DNA is digested with a restriction endonuclease and size separated by gel electrophoresis. Hybridizations typically occur with the target sequence bound to the surface of a membrane or, as described in U.S. Pat. No. 5,468,613, the ASH probe sequence may be bound to a membrane.

ASH data are typically obtained by amplifying nucleic acid fragments (amplicons) from genomic DNA using PCR, transferring the amplicon target DNA to a membrane in a dot-blot format, hybridizing a labeled oligonucleotide probe to the amplicon target, and observing the hybridization dots by autoradiography.

Isozyme markers can be employed as genetic markers, e.g., to track markers other than the reduced levels of saturated fatty acid markers herein, or to track isozyme markers linked to the markers herein. Isozymes are multiple forms of enzymes that differ from one another in their amino acid, and therefore their nucleic acid sequences. Some isozymes are multimeric enzymes containing slightly different subunits. Other isozymes are either multimeric or monomeric but have been cleaved from the proenzyme at different sites in the amino acid sequence. Isozymes can be characterized and analyzed at the protein level, or alternatively, isozymes which differ at the nucleic acid level can be determined. In such cases any of the nucleic acid based methods described herein can be used to analyze isozyme markers.

In some examples, a nucleic acid probe is used to detect a nucleic acid that comprises a marker sequence. Such probes can be used, for example, in positional cloning to isolate nucleotide sequences linked to the marker nucleotide sequence. The nucleic acid probes are not limited to any particular size. In some examples, nucleic acid probe is at least 20 nucleotides in length, at least 50 nucleotides in length, at least 100 nucleotides in length, at least 200 nucleotides in length or greater. A hybridized probe is detected using, autoradiography, fluorography or other similar detection techniques depending on the label to be detected. Examples of specific hybridization protocols are widely available in the art.

In general, synthetic methods for making oligonucleotides, including probes, primers, molecular beacons, PNAs, LNAs (locked nucleic acids), etc., are well known. For example, oligonucleotides can be synthesized chemically according to the solid phase phosphoramidite triester method described by Beaucage and Caruthers (1981), *Tetrahedron Letts.,* 22(20): 1859-1862, e.g., using a commercially available automated synthesizer, e.g., as described in Needham-VanDevanter et al. (1984) *Nucleic Acids Res.,* 12:6159-6168. Any nucleic acid can be custom ordered from any of a variety of commercial sources, such as The Midland Certified Reagent Company, The Great American Gene Company, ExpressGen Inc., Operon Technologies Inc. (Alameda, Calif.) and many others. Similarly, PNAs can be custom ordered from any of a variety of sources, such as PeptidoGenic, HTI Bio-Products, Inc., BMA Biomedicals Ltd (U.K.), Bio•Synthesis, Inc., and many others.

In some examples, in silico methods can be used to detect the marker loci of interest. For example, the sequence of a nucleic acid comprising the marker locus of interest can be stored in a computer. The desired marker locus sequence or its homolog can be identified using an appropriate nucleic acid search algorithm as provided by, for example, in such readily available programs as BLAST, or even simple word processors.

The KASPar® and Illumina® Detection Systems are additional examples of commercially-available marker detection systems. KASPar® is a homogeneous fluorescent genotyping system which utilizes allele specific hybridization and a unique form of allele specific PCR (primer extension) in order to identify genetic markers (e.g. a SNP associated with reduced levels of saturated fatty acids). The assays utilize DNA markers on a plate or variable platform that hybridize target DNA, signaling the presence or absence of a particular marker (e.g. a SNP associated with reduced levels of saturated fatty acids). These systems allow for detection of a large number of genetic markers in a single assay which can be tailored to a specific marker or set of markers. Illumina® detection systems utilize similar technology in a fixed platform format. The fixed platform utilizes a physical plate that can be created with up to 384 markers (e.g. a SNP associated with reduced levels of saturated fatty acids). The Illumina® system is created with a single set of markers that cannot be changed and utilizes dyes to indicate marker detection. These systems represent a wide variety of available detection systems which can be utilized to detect the SNP associate with reduced levels of saturated fatty acids. Other detection systems can also be used.

It will be appreciated that although specific examples of primers are provided herein, additional primers and/or primer pairs can be designed using any suitable method and are encompassed by the teachings herein. For example, primers can be designed using any suitable software program, such as LASERGENE®.

In some examples, the primers are radiolabelled, or labeled by any suitable means (e.g., using a non-radioactive fluorescent tag), to allow for rapid visualization of the different size amplicons following an amplification reaction without any additional labeling step or visualization step. In some examples, the primers are not labeled, and the amplicons are visualized following their size resolution, e.g., following agarose gel electrophoresis. In some examples, ethidium bromide staining of the PCR amplicons following size resolution allows visualization of the different size amplicons.

The primers are not limited to primers generating an amplicon of any particular size. For example, the primers used to amplify the marker loci and alleles herein are not limited to amplifying the entire region of the relevant locus. The primers can generate an amplicon of any suitable length that is longer or shorter than those given in disclosed sequences. In some examples, marker amplification produces an amplicon at least 20, 50, 100, 200, 250, 300, 350, 400, 450, 500, 550, 600, 650, 700, 750, 800, 850, 900, 950, 1000, or more nucleotides in length.

Development of molecular markers in crop species facilitates the potential for increased efficiency in plant breeding through marker assisted selection (MAS). Genetic markers are used to identify plants that contain a desired genotype at one or more loci, and that are expected to transfer the desired genotype, along with a desired phenotype to their progeny. Genetic markers can be used to identify plants that contain a desired genotype at one locus, or at several unlinked or linked loci (e.g., a haplotype), and that would be expected to transfer the desired genotype, along with a desired phenotype to their progeny. The means to identify plants, particularly soybean plants, having reduced levels of saturated fatty acids by identifying plants having a specified allele defined by the SNP allele of SEQ ID NO: 1 or the SNP allele SEQ ID NO: 2 are provided.

Similarly, by identifying plants lacking the desired SNP, plants with wild-type levels of saturated fatty acids can be identified and, e.g., eliminated from subsequent crosses or selected for if wild-type levels of fatty acids are desired. Similarly, these marker loci can be introgressed into any desired genomic background, germplasm, plant, line, variety, etc., as part of an overall MAS breeding program.

Marker-assisted selection (MAS) can be used to select plants that contain the marker allele (or alleles) that correlate with the desired phenotype. In brief, a nucleic acid corresponding to the marker nucleic acid allele is detected in a biological sample from a plant to be selected. This detection can take the form of hybridization of a probe nucleic acid to a marker allele or amplicon thereof, e.g., using allele-specific hybridization, Southern analysis, northern analysis, in situ hybridization, hybridization of primers followed by PCR amplification of a region of the marker, or the like. A variety of procedures for detecting markers are described herein. After the presence (or absence) of a particular marker allele in the biological sample is verified, the plant is selected, e.g., used to make progeny plants by selective breeding.

Soybean plant breeders desire combinations of reduced levels of saturated fatty acid traits with genes for high yield and other desirable traits to develop improved soybean varieties. Screening large numbers of samples by non-molecular methods (e.g., trait evaluation in soybean plants) can be expensive, time consuming, and unreliable. Use of the polymorphic markers described herein provides an effective method for selecting resistant varieties in breeding programs. For example, one advantage of marker-assisted selection over field evaluations for reduced levels of saturated fatty acids is that MAS can be done at any time of year, regardless of the growing season. Moreover, environmental effects are largely irrelevant to marker-assisted selection.

One application of MAS is to use the markers for reduced saturated fatty acid level to increase the efficiency of an introgression or backcrossing effort aimed at introducing reduced levels of saturated fatty acids into a desired background, for example a high yielding soybean line. In marker assisted backcrossing of specific markers from a donor source, e.g., to an elite or exotic genetic background, one selects among backcross progeny for the donor trait, and then uses repeated backcrossing to the elite or exotic line to reconstitute as much of the elite/exotic background's genome as possible.

Thus, the markers and methods provided can be utilized to guide marker assisted selection or breeding of soybean varieties with the desired complement (set) of allelic forms of chromosome segments associated with reduced levels of saturated fatty acids. Any of the disclosed marker alleles can be introduced into a soybean line via introgression, by traditional breeding (or introduced via transformation, or both) to yield a soybean plant with superior agronomic performance. The number of alleles associated with reduced levels of saturated fatty acids that can be introduced or be present in a soybean plant ranges from 1 to the number of alleles disclosed herein, each integer of which is incorporated herein as if explicitly recited.

Also provided are methods of making a progeny soybean plant and these progeny soybean plants, per se. The methods comprises crossing a first parent soybean plant with a second soybean plant and growing the female soybean plant under plant growth conditions to yield soybean plant progeny. Methods of crossing and growing soybean plants are well within the ability of those of ordinary skill in the art. Such soybean plant progeny can be assayed for alleles associated with reduced levels of saturated fatty acids and, thereby, the desired progeny selected. Such progeny plants or seed can be sold commercially for soybean production, used for food, processed to obtain a desired constituent of the soybean, or further utilized in subsequent rounds of breeding. At least one of the first or second soybean plants is a soybean plant of the present invention in that it comprises at least one of the allelic forms of the markers, such that the progeny are capable of inheriting the allele.

Often, the methods are applied to at least one related soybean plant such as from progenitor or descendant lines in the subject soybean plants pedigree such that inheritance of the desired reduced levels of saturated fatty acid allele can be traced. The number of generations separating the soybean plants being subjected to the methods will generally be from 1 to 20, commonly 1 to 5, and typically 1, 2, or 3 generations of separation, and quite often a direct descendant or parent of the soybean plant will be subject to the method (i.e., one generation of separation).

Genetic diversity is important for long term genetic gain in any breeding program. With limited diversity, genetic gain will eventually plateau when all of the favorable alleles have been fixed within the elite population. One objective is to incorporate diversity into an elite pool without losing the genetic gain that has already been made and with the minimum possible investment. MAS provide an indication of which genomic regions and which favorable alleles from the original ancestors have been selected for and conserved over time, facilitating efforts to incorporate favorable variation from exotic germplasm sources (unrelated to the elite gene pool) to find favorable alleles that do not currently exist in the elite gene pool. For example, the markers can be used for MAS in crosses of elite soybean lines×exotic soybean lines by subjecting the segregating progeny to MAS analysis to maintain or incorporate existing desired trait(s), along with the reduced levels of saturated fatty acid marker alleles herein.

EXAMPLES

The following examples are offered to illustrate, but not to limit, the claimed invention. It is understood that the examples and embodiments described herein are for illustrative purposes only, and persons skilled in the art will recognize various reagents or parameters that can be altered without departing from the spirit of the invention or the scope of the appended claims.

Fap3 is a locus contributing to reduction of palmitic acid (16:0), one of the significant saturated fatty acids in soybean. Soybean line A22 was developed by treatment of seeds of A1937 with N-nitrosomethylurea (NMU) and contains the single recessive allele for fap3 (Fehr et al. (1991) Crop Sci 31:88-89; Schnebly et al. (1994) Crop Sci 34:829-833). Pioneer soybean line 92B72 contains both the fap1 mutation from C1726 and the fap3 mutation from A22. DNA was isolated from soybean lines 92B72, C1726, 93B82, and Williams82 using a standard urea extraction method. Primers for the FatB1a gene (Cardinal et al. (2007) Crop Sci 47:304-310) were used for PCR followed by Sanger sequencing of the amplicons to identify SNPs in the gene. 15 SNPs were identified between these lines. In 14 of these SNPs, Williams82 contained the same allele as 92B72. One SNP was unique in the four lines, and was determined to be derived from soybean line 92B72. Taqman™ assays for allelic discrimination were developed for 3 SNPs, including the SNP unique to 92B72. Assays were then tested on a population following standard Taqman™ conditions.

Genomic DNA Extraction Using Urea:
1. Grind 2 g fresh tissue or 0.5 g lyophilized tissue and add it to 6 mL urea extraction buffer and mix well.
2. Add RNase A (100 mg/mL) and incubate @ 37° C. for 20 min.
   a. 30 µL—Leaf
   b. 12 µL—Seed
3. Add 4-5 mL Phenol:Chloroform:Isoamyl 25:24:1. Mix well. (Sigma P3803)
4. Put on rocker inside hood.
   a. Fresh—15 min
   b. Lyophilized—30 min
5. Centrifuge @ 8000 rpm at 10° C. for 10 min.
6. Transfer supernatant to clean tube.
7. Add 700 µL of 3M NaOAC (pH 5.0) and 5 mL cold isopropanol. Mix well.
8. Hook DNA and wash in 70% EtOH.
9. Repeat 70% EtOH wash.
10. Transfer pellet to 1.5 mL tube and allow to dry.
11. Dissolve pellet in 1 mL 10 mM Tris.

7 M Urea Extraction Buffer:

| Water | 350 mL |
| Urea | 336 g |
| 5M NaCl | 50 mL (14.61 g) |
| 1M Tris | 40 mL (pH 8.0) |
| .5M EDTA | 32 mL (pH 8.0) |
| 20% Sarcosine Sol. | 40 mL (8 g) |

Adjust volume to 800 mL with ddH2O

SNP PCR Reaction/Conditions:

| PCR Reaction Mix (SNP Discovery) | |
| --- | --- |
| Reagent | 1X (µL) |
| gDNA (~20 ng/µl) | 5.0 |
| 10x PCR Buffer | 2.0 |
| 1 mM dNTP | 2.0 |
| Taq | 0.1 |
| 1 µM Primer (F + R) | 4.0 |
| ddH2O | 6.9 |
| Total | 20.0 |

| PCR Conditions | | | |
| --- | --- | --- | --- |
| Step | Temp | Time | #Cycles |
| initial denature | 95° C. | 3 min | 1X |
| denature | 95° C. | 50 sec | 35X |
| anneal | 52° C. | 50 sec | |
| extension | 72° C. | 85 sec | |
| final extension end | 72° C. | 10 min | 1X |

Taqman™ Assay Reaction/Conditions

| Reagent | Vol (µl) |
| --- | --- |
| H2O | 3.625 |
| Hottub buffer | 0.5 |
| dNTP (2.5 mM each) | 0.375 |
| primer 1 + primer 2 (10 µM each) | 0.15 |
| primer 3 + primer 4 (10 µM each) | 0.15 |
| probe 1 (10 µM) | 0.05 |
| Probe 2 (10 µM) | 0.05 |
| Hottub enzyme | 0.025 |
| Invitrogen rox dye (50X) | 0.075 |
| DNA (16 ng total) | 0.05 |
| Total | 5.05 |

| PCR Conditions | | | |
| --- | --- | --- | --- |
| Step | Temp | Time | #Cycles |
| initial denature | 94° C. | 2 min | 1X |
| denature | 94° C. | 30 sec | 40X |
| anneal | 60° C. | 60 sec | |
| extension end | 72° C. | 1 sec | |

Figure 3:
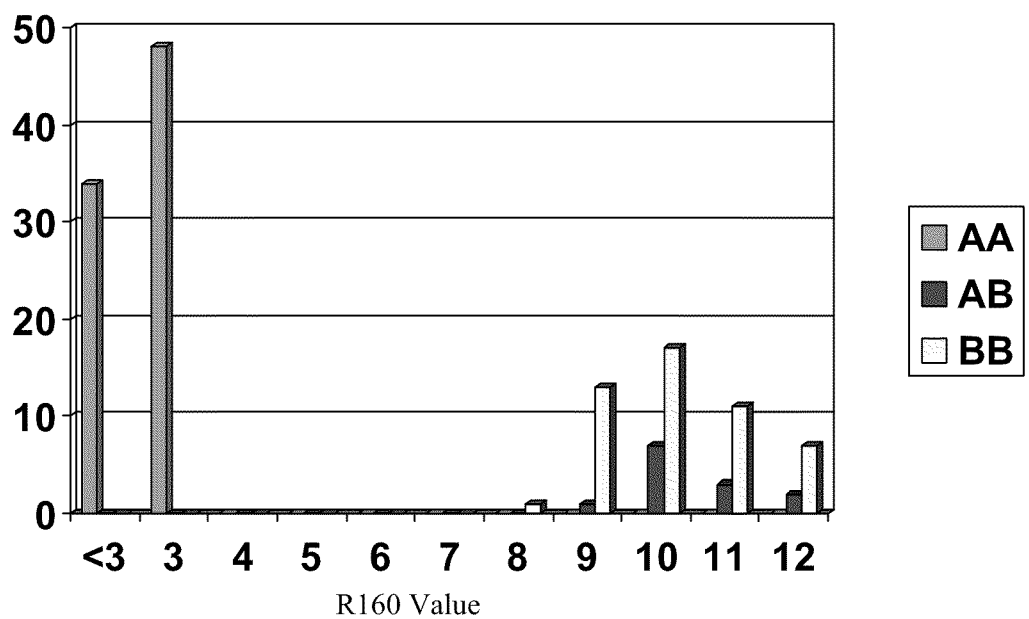
FIG. 3: Histogram of the data from FIG. 2. This demonstrates the clear separation of the low palmitic acid content individuals with the favorable alleles and the wild-type (normal) concentrations of palmitic acid in the individuals. The y-axis reflects the count in each percentage bin.

After the relevant SNP was identified from line 92B72, several lines were analyzed for their genotype at the SNP of interest and correlated to the presence or absence of the low saturated fatty acid phenotype (R160). These results are summarized in FIGS. 1 and 2, with FIG. 1 provides a scatterplot of the correlation between the SNP of interest and the phenotype of interest and FIG. 2 showing the detailed results from the analysis. These results are further illustrated in FIG. 3 and summarized in FIG. 4. As shown by these data, the SNP discovered is strongly predictive of the presence or absence of the low sat phenotype in soybean across a multitude of populations.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations. All publications, patents, patent applications, and/or other documents cited in this application are incorporated by reference in their entirety for all purposes to the same extent as if each individual publication, patent, patent application, and/or other document were individually indicated to be incorporated by reference for all purposes.

We claim:

1. A method of identifying a soybean plant with reduced levels of saturated fatty acid, the method comprising:
   (a) isolating nucleic acids from a soybean plant;
   (b) using the isolated nucleic acids to detect an allele comprising a nucleotide polymorphism at Gm05:7995435, wherein the nucleotide polymorphism is an A, and is associated with reduced levels of palmitic acid; and
   (c) selecting the soybean plant having the allele associated with reduced levels of saturated fatty acid.

2. The method of claim 1, further comprising breeding the selected soybean plant with a second soybean plant.

3. The method of claim 1, wherein said soybean plant is derived from variety 92B72.

4. The method of claim 1, wherein said allele is identified by SEQ ID NO:1.

5. The method of claim 1, wherein the allele is detected by allele specific hybridization.

6. The method of claim 1, wherein said allele is located within a protein coding region.

7. The method of claim 6, wherein said allele is located within the protein coding region for the Fap3 (FATB1a) gene.

8. The method of claim 1, wherein detecting comprises amplifying a marker locus comprising the allele and detecting the resulting amplicon.

9. The method of claim 8, wherein the amplifying comprises:
   (a) admixing an amplification primer or amplification primer pair with a nucleic acid isolated from the soybean plant, wherein the primer or primer pair is complementary or partially complementary to at least a portion of the marker locus, and is capable of initiating DNA polymerization by a DNA polymerase using the soybean nucleic acid as a template; and
   (b) extending the primer or primer pair in a DNA polymerization reaction comprising the DNA polymerase and the soybean template nucleic acid to generate at least one amplicon.

10. The method of claim 9, wherein the marker locus is amplified using primers SEQ ID NOs: 5 and 6, SEQ ID NOs: 8 and 9, or SEQ ID NOs: 11 and 12.

11. The method of claim 9, wherein the amplicon is detected using SEQ ID NO:3, SEQ ID NO: 4, or a combination of SEQ ID NO: 3 and 4 as a probe.

12. The method of claim 1, wherein said allele is located on soybean (*Glycine max*) chromosome 5.

* * * * *

SEQUENCE LISTING

<160> NUMBER OF SEQ ID NOS: 12

<210> SEQ ID NO 1
<211> LENGTH: 1120
<212> TYPE: DNA
<213> ORGANISM: Glycine max

<400> SEQUENCE: 1

```
gacatagttc aagtggacac ttgggtttct ggatcaggga agaatggtat gcgccgtgat    60
ttgcttttac gtgactgcaa aactggtgaa atcttgacaa gagcttccag gtagaaatca   120
ttctctggaa ttttccttcc cctttccttc tgcttcaagc aaattttaag atgtgtatct   180
taatgtactt gatggtgatt gggcacaatt ttgaatcttc catacatttt aaaagttatg   240
gaacccttc ttttccttct taagatgcaa atttgtcatg actgaagttt caggtaatca   300
tttgcatttt gcagtgttaa aaaagataat gaactcacaca tttattatat tttgcaggca   360
aaaacctcta attaaacaaa ctgaacattg tatcttagtt tatttatcag actttatcat   420
gtgtactgat gcatcacctt ggagcttgta atgaattaca tattagtatt ttctgaactg   480
tttgttatgg ttttggtgat ctacagtgtt tgggtcatga tgaataagct aacacggagg   540
ctgtctaaaa ttccagaaga agtcagacag gagataggat cttatttttgt ggattctgat   600
ccaattctgg aagaggataa cagaaaactg actaaacttg acgacaacac agcggattat   660
attcgtaccg gtttaagtgt atgtcaacta gttttttttc taattgctgt cattaattta   720
ttttctcaaa ttatttcaga tgttgttttc taattagttt acataatgca tcttcatttt   780
gcagcctagg tggagtgatc tagatatcaa tcagcatgtc aacaatgtga agtacattgg   840
ctggattctg gaggtatttt tctgttcttg tattctaatc aactgcaatc catgttagtt   900
ctttaaccaa aggactgtct tttgattgtt gcagagtgct ccacagccaa tcttggagag   960
tcatgagctt tcttccatga ctttagagta taggagagag tgtggtaggg acagtgtgct  1020
ggattccctg actgctgtat ctggggccga catgggcaat ctagctcaca gcgggcatgt  1080
tgagtgcaag catttgcttc gactggaaaa tggtgctgag                        1120
```

<210> SEQ ID NO 2
<211> LENGTH: 1120
<212> TYPE: DNA
<213> ORGANISM: Glycine max

<400> SEQUENCE: 2

```
gacatagttc aagtggacac ttgggtttct ggatcaggga agaatggtat gcgycgtgat    60
tggcttttac gtgactgcaa aactggtgaa atcttgacaa gagcttccag gtagaaatca   120
ttctctggaa ttttccttcc cctttccttc tgcttcaagc aaattttaag atgtgtatct   180
taatgtactt gatggtgatt gggcacaatt ttgaatcttc catacatttt aaaagttatg   240
gaacccttc ttttccttct taagatgcaa atttgtcatg actgaagttt caggtaatca   300
tttgcatttt gcagtgttaa aaaagataat gaactcacaca tttattatat tttgcaggca   360
aaaacctcta attaaacaaa ctgaacattg tatcttagtt tatttatcag actttatcat   420
gtgtactgat gcatcacctt ggagcttgta atgaattaca tattagtatt ttctgaactg   480
tttgttatgg ttttggtgat ctacagtgtt tgggtcatga tgaataagct aacacggagg   540
ctgtctaaaa ttccagaaga agtcagacag gagataggat cttatttttgt ggattctgat   600
ccaattctgg aagaggataa cagaaaactg actaaacttg acgacaacac agcggattat   660
```

```
attcgtaccg gtttaagtgt atgtcaacta gttttttttc taattgctgt cattaattta      720
ttttctcaaa ttatttcaga tgttgttttc taattagttw acataatgca tcttcatttt      780
gcagcctagg tggagtgatc tagatatcaa tcagcatgtc aacaatgtga agtacattgg      840
ctggattctg gaggtatttt tctgttcttg tattctaatc aactgcaatc catgttagtt      900
ctttaaccaa aggactgtct tttgattgtt gcagagtgct ccacagccaa tcttggagag      960
tcatgagctt tcttccatga ctttagagta taggagagag tgtggtaggg acagtgtgct     1020
ggattccctg actgctgtat ctggggccga catgggcaat ctagctcaca gcgggcatgt     1080
tgagtgcaag catttgcttc gactggaaaa tggtgctgag                            1120

<210> SEQ ID NO 3
<211> LENGTH: 15
<212> TYPE: DNA
<213> ORGANISM: Artificial Sequence
<220> FEATURE:
<223> OTHER INFORMATION: FAM probe S04257-1-P1

<400> SEQUENCE: 3
taaaagcaaa tcacg                                                         15

<210> SEQ ID NO 4
<211> LENGTH: 13
<212> TYPE: DNA
<213> ORGANISM: Artificial Sequence
<220> FEATURE:
<223> OTHER INFORMATION: VIC probe S04257-1-P2

<400> SEQUENCE: 4
aaagccaatc acg                                                           13

<210> SEQ ID NO 5
<211> LENGTH: 22
<212> TYPE: DNA
<213> ORGANISM: Artificial Sequence
<220> FEATURE:
<223> OTHER INFORMATION: Forward primer S04257-F1

<400> SEQUENCE: 5
caagatttca ccagttttgc ag                                                 22

<210> SEQ ID NO 6
<211> LENGTH: 20
<212> TYPE: DNA
<213> ORGANISM: Artificial Sequence
<220> FEATURE:
<223> OTHER INFORMATION: Reverse primer S04257-R1

<400> SEQUENCE: 6
gtggacactt gggtttctgg                                                    20

<210> SEQ ID NO 7
<211> LENGTH: 766
<212> TYPE: DNA
<213> ORGANISM: Glycine max

<400> SEQUENCE: 7
ggaaggaaaa ttccagagaa tgatttctac ctggaagctc ttgtcaagat ttcaccagtt       60
ttgcagtcac gtaaaagcca atcacgacgc ataccattct tccctgatcc agaaacccaa      120
gtgtccactt gaactatgtc acccctgaag caaatataga cacacaattt cagataatta      180
gatttagaat aaccataata atactaatag cttatctaac ttcaacccaa caccaagaag      240
```

```
tcagaataat tgcattcttt atacatctag tagtactcaa acagaacaga gggtatatat    300
aactggtaag aaaacaaatg caaagaatac atagtatcag cttctatttt tacaataatt    360
aaacaaggat aagtcacctt atctaataac atgtaattaa tgctatacta catctcttgt    420
acagatcaat agctctgttg cacaaggttt cccatagttc atcatgtata aagcttgtgt    480
atctaatcaa ttttcatccc agacaaattt ccaaagcatt ttggttctca taattaagtc    540
tcaataatta ccatgaatat atttaggagt gatcattcct cataaagatt actaaaatag    600
acagagaaat agcagcttaa catggataca ttgcaaatca catgtaatgg ttgaatctag    660
atgactaacc atgtaggata gcgttccacc acaacctgca tccgagtaac cacccatatc    720
aagttctttt tgcacatttc tggcgtggaa ccaaagactg gccgtc                   766
```

<210> SEQ ID NO 8
<211> LENGTH: 22
<212> TYPE: DNA
<213> ORGANISM: Artificial Sequence
<220> FEATURE:
<223> OTHER INFORMATION: S04257-F3 forward primer for S04257-1-B

<400> SEQUENCE: 8

```
gatttcacca gttttgcagt ca                                              22
```

<210> SEQ ID NO 9
<211> LENGTH: 20
<212> TYPE: DNA
<213> ORGANISM: Artificial Sequence
<220> FEATURE:
<223> OTHER INFORMATION: S04257-R3 Reverse primer for S04257-1-B

<400> SEQUENCE: 9

```
gggtttctgg atcagggaag                                                 20
```

<210> SEQ ID NO 10
<211> LENGTH: 766
<212> TYPE: DNA
<213> ORGANISM: Glycine max

<400> SEQUENCE: 10

```
ggaaggaaaa ttccagagaa tgatttctac ctggaagctc ttgtcaagat ttcaccagtt     60
ttgcagtcac gtaaaagcca atcacgacgc ataccattct tccctgatcc agaaacccaa    120
gtgtccactt gaactatgtc acccctgaag caaatataga cacacaattt cagataatta    180
gatttagaat aaccataata atactaatag cttatctaac ttcaacccaa caccaagaag    240
tcagaataat tgcattcttt atacatctag tagtactcaa acagaacaga gggtatatat    300
aactggtaag aaaacaaatg caaagaatac atagtatcag cttctatttt tacaataatt    360
aaacaaggat aagtcacctt atctaataac atgtaattaa tgctatacta catctcttgt    420
acagatcaat agctctgttg cacaaggttt cccatagttc atcatgtata aagcttgtgt    480
atctaatcaa ttttcatccc agacaaattt ccaaagcatt ttggttctca taattaagtc    540
tcaataatta ccatgaatat atttaggagt gatcattcct cataaagatt actaaaatag    600
acagagaaat agcagcttaa catggataca ttgcaaatca catgtaatgg ttgaatctag    660
atgactaacc atgtaggata gcgttccacc acaacctgca tccgagtaac cacccatatc    720
aagttctttt tgcacatttc tggcgtggaa ccaaagactg gccgtc                   766
```

<210> SEQ ID NO 11
<211> LENGTH: 23
<212> TYPE: DNA

```
<213> ORGANISM: Artificial Sequence
<220> FEATURE:
<223> OTHER INFORMATION: S04257-F4 Forward primer for S04257-1-C

<400> SEQUENCE: 11
ggaaggaaaa ttccagagaa tga                                           23

<210> SEQ ID NO 12
<211> LENGTH: 20
<212> TYPE: DNA
<213> ORGANISM: Artificial Sequence
<220> FEATURE:
<223> OTHER INFORMATION: S04257-R4 Reverse Primer for S04257-1-C

<400> SEQUENCE: 12
tggacacttg ggtttctgga                                               20
```